(12) United States Patent
Pentkovski

(10) Patent No.: US 7,512,498 B2
(45) Date of Patent: Mar. 31, 2009

(54) STREAMING PROCESSING OF BIOLOGICAL SEQUENCE MATCHING

(75) Inventor: Vladimir M. Pentkovski, Folsom, CA (US)

(73) Assignee: Intel Corporation, Santa Clara, CA (US)

( * ) Notice: Subject to any disclaimer, the term of this patent is extended or adjusted under 35 U.S.C. 154(b) by 542 days.

(21) Appl. No.: 10/331,334

(22) Filed: Dec. 31, 2002

(65) Prior Publication Data
US 2004/0128291 A1 Jul. 1, 2004

(51) Int. Cl.
*G01N 33/48* (2006.01)
(52) U.S. Cl. .............................. 702/20; 712/220; 707/6
(58) Field of Classification Search ............... 707/3; 702/19, 20; 711/122
See application file for complete search history.

(56) References Cited

U.S. PATENT DOCUMENTS

| 5,829,025 | A | * | 10/1998 | Mittal | 711/122 |
| 5,873,052 | A | * | 2/1999 | Sharaf | 702/20 |
| 6,223,276 | B1 | * | 4/2001 | Lee et al. | 712/207 |
| 2003/0046511 | A1 | * | 3/2003 | Buch et al. | 712/1 |

FOREIGN PATENT DOCUMENTS

WO WO 99/50752 * 10/1999

OTHER PUBLICATIONS

Parsons et al., Bioinformatics, vol. 16, pp. 313-325. 2000.*
Microsoft Press, Microsoft Computer Dictionary, 5th edition, pp. 122 and 406, 2002.*
Mano M., Computer System Architecture, 3rd edition, Prentice-Hall, Inc., pp. 93-103, 1993.*
Rognes et al., Bioinformatics, vol. 16, pp. 699-706, 2000.*
Computer Dictionary, Third Edition, Microsoft Press, 1997, pp. 367 and 419.*
Singh et al., A Scalable Systolic Multiprocessor System for Analysis of Biological Sequences, Proc. Symp. On Integrated Systems, 1993, pp. 168-182.*
Hirschberg et al., Kestrel: A Programmable Array for Sequence Analsysis, Proc. Int. Conf. Application-Specific Systems, Architectures, and Processors, IEEE CS, Aug. 19-21, 1996, pp. 25-34.*
Schmidt et al., V. PaCT 2001, V. Malyshkin (Ed.) LNCS 2127, pp. 498-509, Jan. 2001.*
Hauser et al., Augmenting a Microprocessory with Reconfigurable Hardware, UC Berkeley, Fall 2000, pp. 1-255.*
Thorncock et al., Proceedings of the 2000 Winter Simulation Conference, 2000, pp. 471-479.*
Huang et al., ISLPED'01, Aug. 6-7, Huntington Beach, California, USA, pp. 10-15, 2001.*

* cited by examiner

*Primary Examiner*—Cheyne D Ly
(74) *Attorney, Agent, or Firm*—Kenyon & Kenyon LLP

(57) ABSTRACT

A data system is provided for biological sequence matching. The system includes a system memory, a cache controller coupled to the system memory, a first cache coupled to the cache controller to receive non-temporal data from the system memory, and a second cache coupled to the cache controller to receive temporal data from the system memory. The first cache to also receive the temporal data from the second cache. The system further includes a processor coupled to the cache controller and the first cache.

12 Claims, 4 Drawing Sheets

STREAMING PROCESSING OF BIOLOGICAL SEQUENCE MATCHING

BACKGROUND OF THE INVENTION

1. Field of the Invention

The present invention relates to biological sequence matching. In particular, the present invention relates to systems and methods for scalable streaming processing of rigorous matching algorithms.

2. Description of Related Art

Biological sequence matching is a computational method for obtaining biological information. Sequence matching is used to determine if a biological sequence belongs to a known family of sequences, such as DNA sequences and protein sequences. In biological sequence matching, a comparison is made of a given sequence, such as a queried sequence, with sequences usually taken from a database of known sequences; for example, GeneBank®, LocusLink and/or UniGene at the National Center for Biotechnology Information at the National Institutes of Health There are two classes of algorithms in biological sequence matching: "rigorous matching algorithms" which perform full combinatorial comparison, and "heuristic matching algorithms'" which reduce the number of comparisons using heuristic processes. Two types of rigorous matching algorithms include Hidden Markov Model (HMM) algorithm and the Smith-Waterman (SW) algorithm. Rigorous matching algorithms, contrary to heuristic matching algorithms, cover all potential combinations, and thus may require high computational complexity and large memory.

BRIEF DESCRIPTION OF THE DRAWINGS

The advantages of the present invention will become more readily apparent to those ordinarily skilled in the art after reviewing the following detailed description and accompanying drawings, wherein.

DETAILED DESCRIPTION OF THE INVENTION

Figure 1:
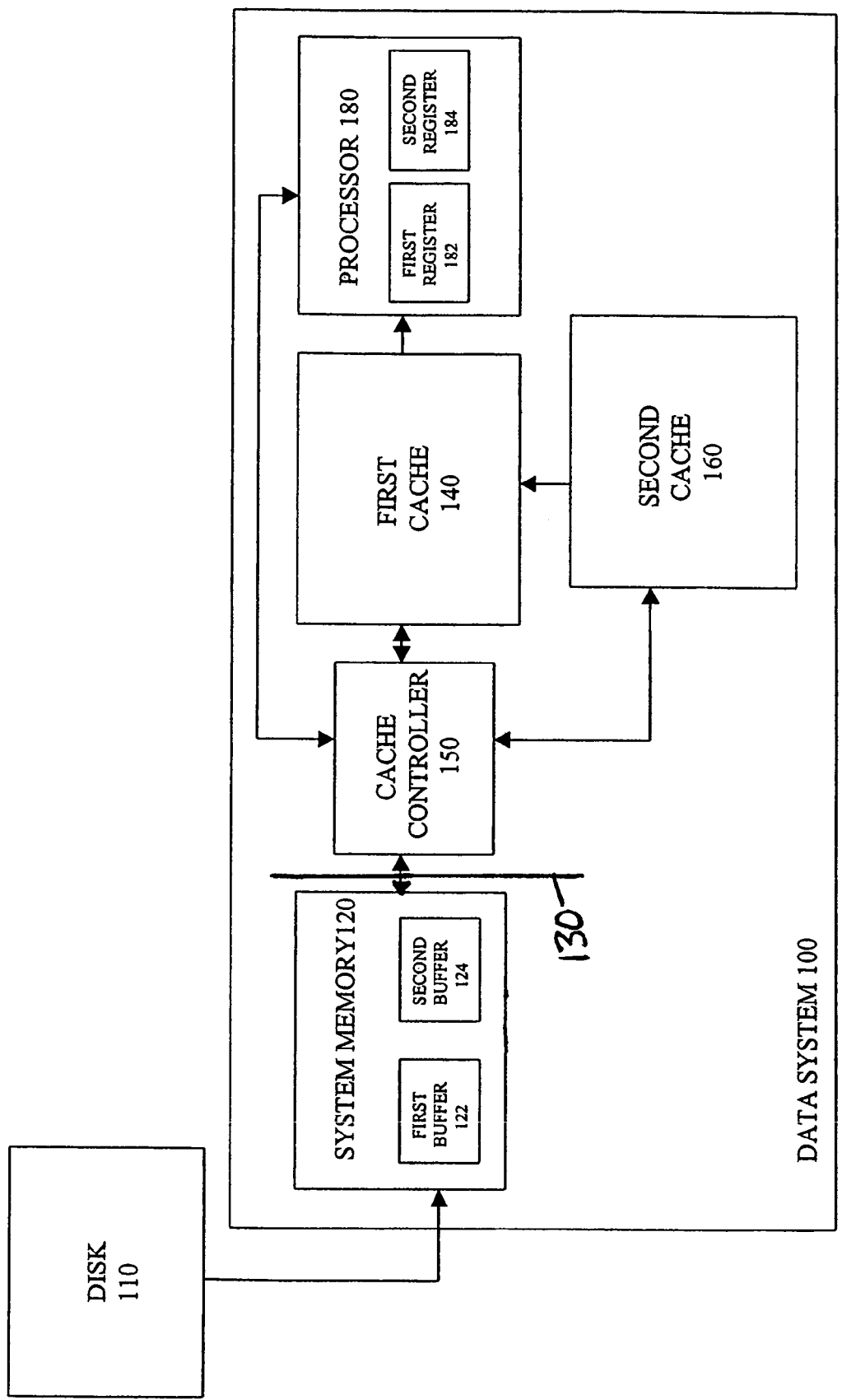
FIG. 1 shows a prior art processor system for processing data from a system memory in accordance with the various embodiments of the present invention.

In accordance with the various embodiments of this invention, a data system, such as a computational system, may be provided for biological sequence matching using rigorous matching algorithms. The various embodiments may include streaming processing of rigorous matching algorithms by overlapping the various stages of processing, and thus achieving more efficient use of the computational system resources. The overlapping stages may include fetching data from disk, fetching data from memory to cache, and processing data that may be present in the cache already.

In accordance with embodiments of the present invention, when data throughput needed to feed computations is less than the maximum effective memory bandwidth, the processing may become computation bound rather than memory bound. That is, the system balance shifts toward high utilization of processor computational power and toward low utilization of memory bandwidth. Thus, in these embodiments, the balance is shifted toward high utilization of high frequency processors, which speeds up the processing of data and reduces the cost of the data system, for example.

Additionally, in the various embodiments of the present invention, small memory footprint, small cache footprint and low disk input/output bandwidth may be obtained. Accordingly, low cost servers and linear scalability in performance with respect to the number of processors in the microprocessor may result. That is, with an increase in the number of processors used, performance is increased linearly. Thus, in these embodiments, if the data throughput needed to feed computations is far less than the system can support, the processing may be characterized as linearly scalable, where the processing input time and the output time increase with respect to an increase in frequency and number of processors.

In accordance with the various embodiments of the present invention, caches may be used in processing the rigorous matching algorithms. A cache is a storage device that is typically smaller and faster than main system memory, and may be used to hold a copy of instructions and data obtained from the main system memory and likely to be needed by a processor coupled to the main system memory. The processor may be an embedded processor, a standalone microprocessor, a central processing unit in a computer, or other processor types.

In accordance with an embodiment of the present invention, the cache may be integrated on the processor. Alternately, the cache may be implemented as an external random access memory (RAM) coupled to the processor, or may be implemented as static random access memory (SRAM), where information is usually stored as a state of a memory element.

In accordance with an embodiment of the present invention, the cache may be randomly accessible and include tags indicating which lines are valid and which lines are invalid. In addition, the cache may be implemented as multiple caches, each having different sizes and response times. In a write operation, for example, data may be transferred from the processor to the fastest cache and to subsequent slower caches and finally to a main system memory. Alternatively, for read operations, data may be transferred to the processor from the fastest cache and from subsequent slower caches.

Embodiments of multiple level cache storage are the Level (L1) and Level 2 (L2) caches of the PENTIUM® series of processors that include but are not limited to the PENTIUM®, the PENTIUM® Pro™, the PENTIUM II™, PENTIUM III™ and PENTIUM® with MMX microprocessors from Intel Corporation of Santa Clara, Calif.

FIG. 1 illustrates a prior art data system for processing data from a main system memory. As shown in FIG. 1, data system 100 may include a main system memory 120, a system bus 130, a first cache 140, a cache controller 150, a second cache 160, and a processor 180.

In accordance with an embodiment of the present invention, as shown in FIG. 1, system memory 120 may be coupled to a disk 110 that may output data to be stored in system memory 120. As shown in FIG. 1, the stored data in system memory 120 may be output to first cache 140 and second cache 160 via system bus 130 and cache controller 150. As described in further detail below, temporal data, that is, data that will be processed multiple times may be output from system memory 120 to the second cache 160 via system bus 130 and cache controller 150. The temporal data may be output from second cache 160 to first cache 140 for use by processor 180. While the temporal data is being output to first cache 140 and second cache 150, non-temporal data, that is, data that will be processed only once, may be output from system memory 120 to first cache 140 via system bus 130 and cache controller 150, bypassing second cache 160. In operation, processor 180 may receive data from first cache 140 and process the received data for output over system bus 130, or for storage back in system memory 120.

In accordance with these embodiments, substantial speed savings may be realized by transferring the data to first cache 140 from second cache 160, rather than to first cache 140 from system memory 120, because, in these embodiments, second cache 160 is much faster than system memory 120.

As shown in FIG. 1, cache controller 150 may be provided between system memory 120 and first cache 140 to control the operation of first cache 140. For example, address comparison may take place in cache controller 150, where cache controller 150 may determine whether an incoming instruction from main system memory 120 "hits" first cache 140, that is the address of the incoming instruction matches one of the valid entries in the cache. Cache controller 150 may determine whether the instruction is cacheable, and whether the instruction may be a load or store instruction. In such case, a cache "miss" may occur when the address of the incoming instruction does not match any valid entries in the cache. First cache 140 may be incorporated into processor 180 or it may be an external circuit coupled to processor 180, as shown in FIG. 1. For example, in accordance with an embodiment of the present invention, in a PENTIUM® III series microprocessor, first cache 140, which is generally called the L1 cache, and cache controller 150 may both be on-die with processor 180.

In an alternate embodiment (not shown), cache controller 150, first cache 140 and second cache 160 may each be coupled to system bus 130 and to processor 180. As such, cache controller 150 may control the output of data from system memory 120 directly to first cache 140 and second cache 160 without the data passing through cache controller 150.

Second cache 160 may also be incorporated into processor 180, or may be a circuit external to processor 180, as shown in FIG. 1. In a PENTIUM® III series microprocessor, second cache 160 is, generally, called the L2 cache and may also be on-die with processor 180.

In FIG. 1, in an embodiment of the present invention, cache controller 150 may also control the operation of second cache 160. In such instance, cache controller 150 may determine whether an instruction from processor 180 "hits" second cache 160.

In other words, does the instruction require data from second cache 160. However, it should be appreciated that the transfer of data from system memory 120 to second cache 160 may occur under the control of a separate second cache controller (not shown).

Data arrays may be input to processor 180 and some may be structured in such a way that they may exhibit temporal locality, that is, the arrays may be processed multiple times, while the remaining arrays may belong to a non-temporal class, that is, the arrays may only be processed only once. In accordance with the various embodiments of the present invention, there may not be any data with mixed behavior where the level of granularity of data temporality is the entire algorithm, and the entire data structure. That is, all elements of an array may be either always temporal or all elements may be always non-temporal.

Data may be prefetched from disk 110 to system memory 120 using, for example, an asynchronous input/output mechanism. In FIG. 1, temporal data may be prefetched from system memory 120 to second cache 160 by cache controller 150. The temporal data may be prefetched from system memory 120 to second cache 160 using Streaming Single Instruction Multiple Data (SIMD) Extensions (SSE™), for example, temporal prefetch instructions.

In FIG. 1, non-temporal data may be prefetched from system memory 120 to first cache 140 by cache controller 150. The non-temporal data may be prefetched from system memory 120 to first cache 140 using, for example, SSE™ non-temporal prefetch instructions In the various embodiments of the present invention, fetching of non-temporal data from disk 110 to system memory 120 and from system memory 120 to first cache 140 or second cache 160, in general, happens only once. As described above, all stages of processing such as fetching data from disk 110 to system memory 120, fetching data from system memory 120 to first cache 140 or second cache 160, and processing data already in first cache 140 or second cache 160, may overlap. In these embodiments, pollution of second cache 160 may be avoided, since the non-temporal data prefetch bypasses second cache 160 and loads the non-temporal data directly in to first cache 140. Thus, the temporal data remains untouched in second cache 160.

In these embodiments, as a result of prefetching the non-temporal data directly into first cache 140 while prefetching temporal data to first cache 140 from second cache 160, the processing speed for data system 100 may reach a "warm cache" performance level. The warm cache performance level may be defined as the level of performance that would be achieved if the needed temporal and the non-temporal data was always present in first cache 140. Accordingly, data may be quickly prefetched to first cache 140. Further, this may allow exclusion of temporal data from the memory bandwidth equation, given the multiple use nature of the temporal data, and thus may provide a significant reduction of memory bandwidth. That is, if the system balance shifts toward high utilization of processor computational power and toward low utilization of memory bandwidth, the data may be processed faster and the cost of the data system may be reduced.

Furthermore, in these embodiments, high hit rate is provided for first cache 140 for the temporal data, the footprint of temporal data, in general, is comparatively small and, thus, low cost systems having a small second cache 160 may be achieved. Thus, in these embodiments, there may be a significant reduction in disk input/output in data system 100. Accordingly, advantages such as low cost servers and linear scalability in performance with respect to the number of processors in the microprocessor may be obtained.

It should be appreciated that the transfer of data to second cache 160 from system memory 120 may be independent of the transfer of data to first cache 140 from second cache 160, and also independent of the input of data to processor 180 from first cache 140. The term "independent" may be defined herein to mean that transfer rates and transfer timing between processor 180 and first cache 140 or second cache 160 and between first cache 140 or second cache 160 and system memory 120 may be decoupled. That is, for example, it may be possible to transfer a second segment of a data stream to processor 180 from first cache 140 before completing a transfer of a first segment of the data stream to second cache 160 from system memory 120. Although the preceding example may occur in boundary conditions, such as when both operations are to the same cache line in which data to second cache 160 may be transferred from system memory 120 and data to first cache 140 may be transferred from second cache 160, the boundary conditions are given merely as an example to emphasize the potential for the decoupling of the data transfers and is not meant to infer such boundary conditions are always present.

In various embodiments of the present invention, double-buffering may be applied to read a database of biological sequences to system memory 120. For example, the biological sequence database may include DNA sequence and/or a protein sequence records from the GenBank® database. In FIG. 1, in accordance with an embodiment of the present invention, in double-buffering, at least two buffers, for example, first buffer 122 and second buffer 124 may be used. First buffer 122 may be used to read the database sequences from disk 110 to system memory 120, while second buffer 124 may be used to read data from system memory 120 to first cache 140 and/or second cache 160 for use by processor 180. Reading the database sequences from disk 110 to system memory 120 and from system memory 120 to first cache 140 and/or second cache 160 for use by processor 180 may occur concurrently.

After the database sequences are read from disk 110 to system memory 120 and the data is read from system memory 120 to caches 140, 160, first buffer 122 and second buffer 124 may reverse their roles. That is, first buffer 122, which may contain the data read from disk 110, may be used to read the data from system memory 120 to first cache 140 and/or second cache 160 for use by processor 180, while second buffer 124 may be used to read data from disk 110 to system memory 120. Thus, the stream of database sequences being fetched from disk 110 may re-use the same memory area of system memory 120. As a result, this allows for only a small memory footprint being needed to supply processor 180 with the stream of database sequences.

In accordance with an embodiment of the present invention, a multi-processor version (not shown) of data system 100 may be implemented by replicating coherent blocks of cache controller 150, first cache 140, second cache 160 and processor 180 and coupling each block to system bus 130. Similarly, in the multiprocessor version, in accordance with another embodiment of the present invention in each block, cache controller 150 may be directly coupled to system bus 130 and processor 180 and first cache 140 and second cache 160 may each be directly coupled to system bus 130. In this embodiment, the data being loaded from system memory 120 to first and second caches 140, 160 may be loaded directly into first and second caches 140, 160 without passing through cache controller 150.

It should be appreciated that, although FIG. 1 shows only two buffers 122, 124 in system memory 120, any number of buffers may be used in accordance with embodiments of the present invention. That is, in order to tolerate fluctuation of bandwidth in data system 100, the number of buffers may be increased beyond two without changing the method of buffer re-use described above.

In various embodiments of the present invention, database system 100 may operate using a significant part of Intel's MMX™ technology. For example, the Intel MMX technology extensions (e.g., SSE™ extensions), which may normally be used in SIMD floating point computations, may have cache control instructions incorporated therein to allow for the fetching of the non-temporal data to first cache 140 while bypassing second cache 160. The use of the MMX™ technology may allow all of the computations in inner loops of the matching algorithms, for example, HMM and/or SW, to be performed in the SIMD-manner. Specifically, packed data formats may enable multiple data elements to be processed in parallel. As a result, the performance of data system 100 may be increased. In various embodiments, the same method may be applied to different SIMD width, and different cache line size.

In embodiments of the present invention, the sequencing or orientation of data processing allows for accumulation of intermediate results of the inner loop computations in registers rather than saving the intermediate results in or restoring intermediate results from system memory 120. As shown in FIG. 1, processor 180 may include a first register 182 and a second register 184, which may accumulate intermediate results of the inner loop computations. Because processor 180 may perform multiple accesses to registers per clock, and the number of accesses to memory 120 may be limited by the architecture of processor 180 to one or two accesses per clock, reducing the number of off-die memory accesses, may improve performance. Therefore, by including first register 182 and second register 184 on-die in processor 180, performance of the data system 100 may be improved.

In various embodiments, in order to increase the performance of the matching algorithms' executions in their respective inner loop computations, unaligned loads may not be used. An "unaligned load" may be defined in these embodiments as a load that loads 64-bit data which crosses the boundary of a cache line, that is, a part of the 64 bits of data is stored in one cache line while another part of the 64 bits of data is stored in another cache line. Since the execution of unaligned loads may add a few additional clocks to the execution time that may reduce the performance of data system 100, unaligned loads may not be used.

However, in accordance with an embodiment of the present invention, in order to exploit the temporal locality of the data, the matching algorithm may use processor affinity to attach a task to a cache, for example, first cache 140 and/or second cache 160. Data may have "temporal locality" with respect to the algorithm used when the algorithm frequently accesses the same data. Further, the matching algorithm may not dispatch the next task until the current task is completed. That is, a form of "green threading" may be used to utilize the temporal locality. In general, green threading may be defined as a threading model that is constructed independently of a native threading model supported by the operating system that is being used.

Figure 2:
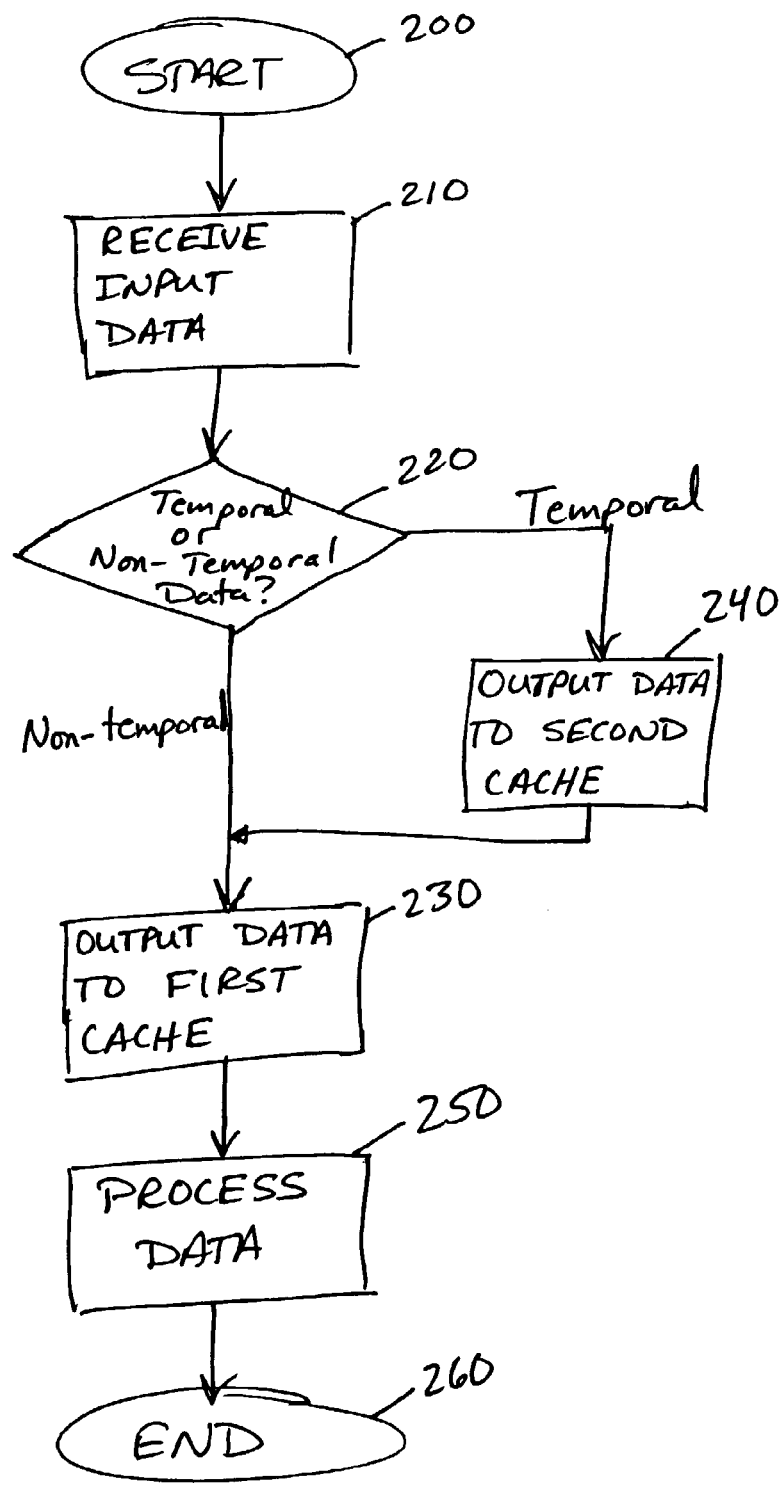
FIG. 2 is a flowchart illustrating a method of data processing, in accordance with an embodiment of the present invention.

FIG. 2 is a flowchart illustrating a method of data processing in accordance with an embodiment of the present invention may be received. In FIG. 2, the method may start (200) and input data may be received (210), for example, the input data may be received (210) in system memory 120 from disk 110 of FIG. 1. Returning to FIG. 2, whether the data is temporal or non-temporal may be determined (220) and the data that is determined (220) to be non-temporal may be output (230) to a first memory, for example, first cache 140 of FIG. 1 from system memory 120.

In FIG. 2, if the data is determined (220) to be temporal, the temporal data may be output (240) to second cache 160 from system memory 120. The temporal data may be output (230) to first cache 140 from second cache 160.

In FIG. 2, the temporal and non-temporal data, may be processed (250) to match the temporal data against all of the non-temporal data by processor 180. Processing (250) of the data may continue until all non-temporal data has been compared, at which time processing may terminate (260).

In accordance with the various embodiments of this invention, the data processing includes biological sequence matching using rigorous matching algorithms. Two types of rigorous matching algorithms include the Smith-Waterman algorithm and the Hidden Markov Model algorithm. In these embodiments, temporal data and non-temporal data may be determined for each of the algorithm, and processed according to the determination results.

In the Smith-Waterman algorithm, database sequences in a database may be compared to a query sequence for example, a DNA query sequence. In accordance with the various embodiments of the present invention, with the Smith-Waterman algorithm, the query sequence may be treated as temporal, since the same query is, generally, being compared to multiple sequences of a database. In addition, arrays of intermediate results and arrays of coefficients may be treated as temporal data and each database sequence may be treated as non-temporal since the database sequence is generally compared to the query sequence only once.

Figure 3:
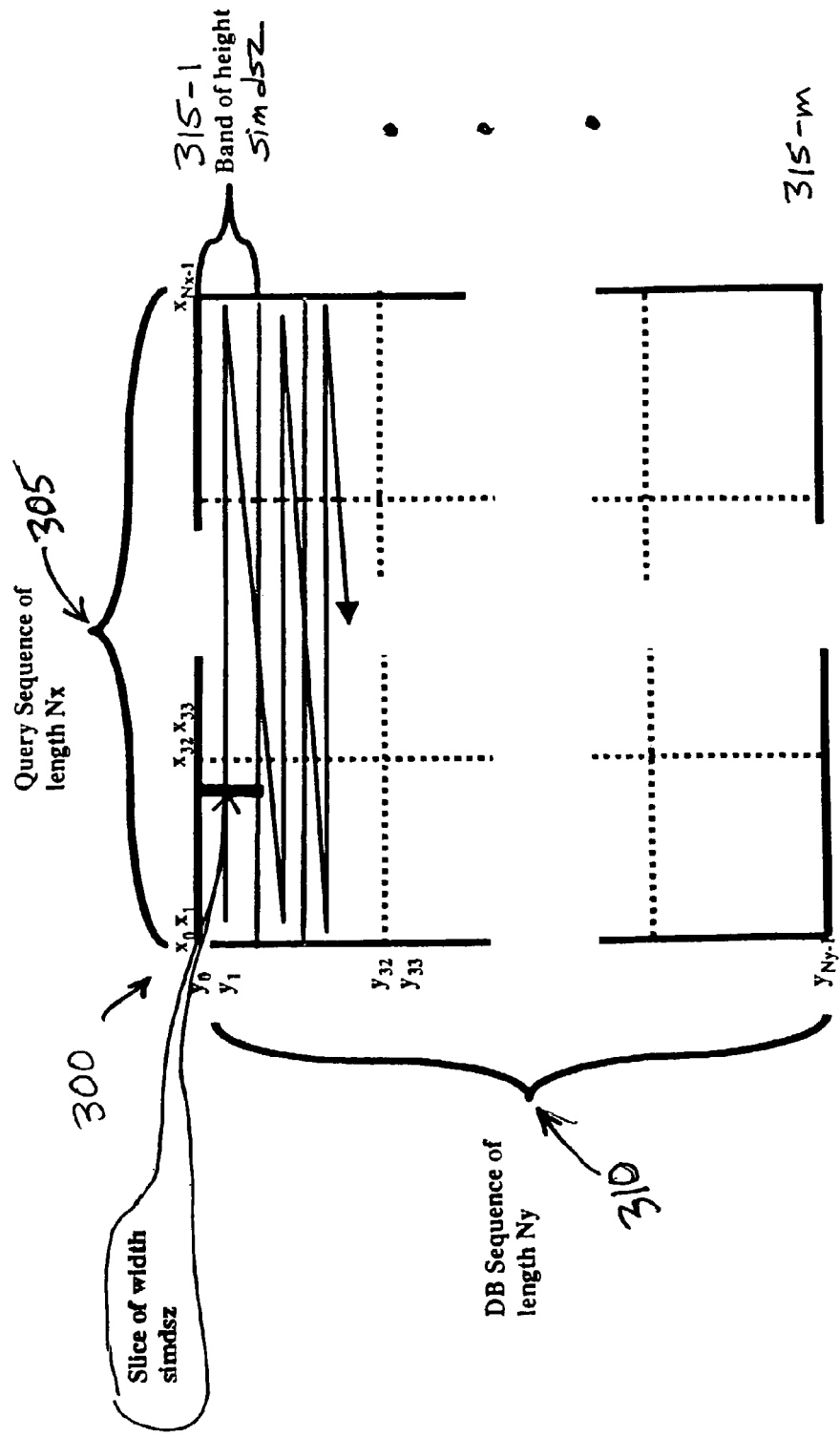
FIG. 3 shows the sequencing of the Smith-Waterman processing, in accordance with an embodiment of the present invention.

FIG. 3 shows the order of comparison in the Smith-Waterman processing, in accordance with an embodiment of the present invention. In FIG. 3, a matrix of the sequences 300 is shown where coordinates $x_0$ to $X_{Nx-1}$ 305 of a query sequence length Nx may extend in the horizontal direction, and coordinates $y_0$ to $y_{Ny-1}$ 310 of a database sequence length Ny may extend in the vertical direction. In FIG. 3, the matrix may be divided into a plurality of bands 315-1 to 315-$m$, where each band may have a length of Nx and a width of simdsz.

As shown in FIG. 3, to compare a database sequence of length Ny with a query sequence of length Nx, a slice of width simdsz of the database sequence and the query sequence may be compared to each other. The comparison may proceed from the left to the right of the band, starting with the top band, and proceeding down to the bottom band with the elements in each slice being processed concurrently.

In general, the Smith-Waterman algorithm may perform a comparison of two sequences, and calculate the similarity score. The score may be the quantitative measure of similarity between the sequences. A mathematical representation of a simplified variation of the Smith-Waterman algorithm, for example, a four times unrolled Smith-Waterman algorithm, may be illustrated as:

$$S(i,j)=\max(S(i-1,j-1)+c(Y_i,X_j),S(i-1,j)-d,S(i,j-1)-d));$$

$$S(i+1,j-1)=\max(S(i,j-2)+c(Y_{i+1},X_{j-1}),S(i,j-1)-d,S(i+1,j-2)-d));$$

$$S(i+2,j-2)=\max(S(i+1,j-3)+c(Y_{i+2},X_{j-2}),S(i+1,j-2)-d,S(i+2,j-3)-d));\text{ and}$$

$$S(i+3,j-3)=\max(S(i+2,j-4)+c(Y_{i+3},X_{j-3}),S(i+2,j-3)-d,S(i+3,j-4)-d)),$$

where:

X and Y are the query and database sequences being matched, respectively;

S is a score matrix that accumulates the similarity score of sequences X and Y. In particular, a score is the measure of similarity between two sequences and the score matrix is used to compute the score. The above formulas describe the process of computation of the matrix elements as a function of previously computed elements of the same matrix;

d is a gap penalty, which is a negative value subtracted from the similarity score if a symbol should be skipped in sequence X or Y in order to continue the comparison; and c is the replacement cost matrix, where element c(i,j) of the cost matrix is equal to the value that should be added to the similarity score if symbol X(i) should be replaced by symbol Y(j)) in order to continue the comparison.

In accordance with an embodiment of the present invention, a top-level pseudo-code representation of the Smith-Waterman algorithm implementation discussed above may be as follows:

```
Initialize processing of query sequence;
For each sequence sx of DB {
    initiate asynchronous read from disk to memory of DB sequence
    following sx;
    check sx read completion and initialize processing of sx;
    for each band bx of sx {
        prefetch next line of sx non-temporally and then tickle it every
        iteration;
        initialize processing of band bx;
        for each slice of bx {
            prefetch next line of query temporally and then tickle it every
            iteration;
            process slice
        }
    }
}
```

"Tickle" refers to a method for retaining a cache line in a cache in a loop intensive algorithm. In operation, the method performs a read of an arbitrary element in the cache line during each iteration of each loop in the algorithm. The element may be any n-bit portion of the cache line, for example, a 32-bit portion. By frequently "tickling," that is "touching", the cache line the method ensures that the cache line will be viewed by the cache controller as most recently used data. As a result, in accordance with an embodiment of the present invention, the cache controller will, generally, consider the line as a lowest priority candidate for cache line replacement.

Likewise, in accordance with an embodiment of the present invention, a detailed pseudo-code representation of the Smith-Waterman algorithm discussed above, with the SSE™ instructions to be used in real code indicated in comments, may be as follows:

Designations linesz—cache line size in bytes. In pseudo code linesz is assumed to be 32, although algorithm is applicable to other sizes simdsz—width of simd in 16b words, In pseudo code simdsz is assumed to be 4, though algorithm is applicable to other sizes char Ybuf0[Ny],Ybuf1[Ny]—buffers for database sequence. Simplifying assumptions: Ny is multiple of line size char *Y—pointer to current buffer char *X[Nx+6]—query sequence of length Nx padded by 6 boundary elements N(0:3) and N(Nx:3). Simplifying assumptions Nx+6 is multiple of line size short Temp[Nx+6]—temporary vector of 16b elements short C[Nal, Nal]—cost matrix of Nal*Nal size, where Nal is size of alphabet, equal to 20 elements for protein. Elements of X and Y are in the range 0 . . . . Nal−1

64b (4×16b) registers $Accum_j$, $ShiftedAccum_{j-2}$, $ShiftedAccum_{j-1}$, CrowInx, CrowDisp, CrowSize, CostDisp, Cost, D Pseudo Code

```
Initialize Temp, D
Initialize processing of query sequence;
For (k=0; k<= Ns−1; k++) {
```

-continued

```
Initiate asynchronous read from disk to empty buffer of DB sequence following k;
Check completion of sequence k read and initialize its processing (Y points to full buffer);
% for each band bx of sx {
    for (i=0; i<=Ny-simdsz; i+=simdsz) {%Ny/4 iterations
        %prefetch next line of sx, and then tickle it every iteration;
        %Non-temporal prefetch of next line of sx;
        non-temporal (Y+i+linesz); %SSE: PREFETCHNTA
        Initialize Accum_j, ShiftedAccum_{j-1}
        %initialize cost computation;
        RowInx=[Y[i+3],Y[i+2],Y[i+1],Y[i]] %load displacement of cost rows in reverse order.
SSE:PEXTRW, PINSRW
        RowDisp=RowInx*CrowSize % compute displacement of rows. SSE: PMULW, PADDW
        Compute row cost displacements for next band and prefetch temporally all lines of cost rows
%SSE: PREFETCHT
        %for each slice of scx process slice
        for (j=3; j<=Nx+5;j++) {%Nx+5 iterations
            %prefetch next line of query, and then tickle it every iteration;
            temporal (X+j+linesz); %SSE: PREFETCHT
            ShiftedAccum_{j-2}=ShiftedAccum_{j-1}
            ShiftedAccum_{j-1}=[Temp[j], Accum[0], Accum[1], Accum[2]] %SSE: PSLL, PINSRW
            CostDisp = RowDisp+X[j-3:simdsx]%[c[X_j,Y_i], c[X_{j-1},Y_{i+1}], c[X_{j-2},Y_{i+2}], c[X_{j-3},Y_{i+3}].
    SSE: PADDW
            Cost_j=[(C+CostDisp(0))*,(C+CostDisp(1))*,(C+CostDisp(2))*,(C+CostDisp(3))*]%SS
            E: PEXTRWL, PINSRW
            Accum_j = max(ShiftedAccum_{j-2}+ Cost_j, Accum-D, ShiftedAccum_{j-1}-D))%SSE:
        PADDSW, PMAXW
            Temp[j-3]=Accum[3]% SSE: PEXTRW
        }
    }
}
```

Similarly, the Hidden Markov Model algorithm may also be used to compare query sequences with sequences in databases. In accordance with the various embodiments of the present invention, if the Hidden Markov Model sequence is matched against a database of sequences to identify the sequences that belong to the family represented by the Hidden Markov Model sequence, the Hidden Markov Model sequence and arrays of intermediate matching results may be treated as temporal while the database sequences may be treated as non-temporal. However, if a database of sequences is matched against a database of Hidden Markov Model sequences to identify the family that the sequence belongs to, the database of sequences may be treated as temporal data while the Hidden Markov Model database sequences may be treated as non-temporal.

Figure 4:
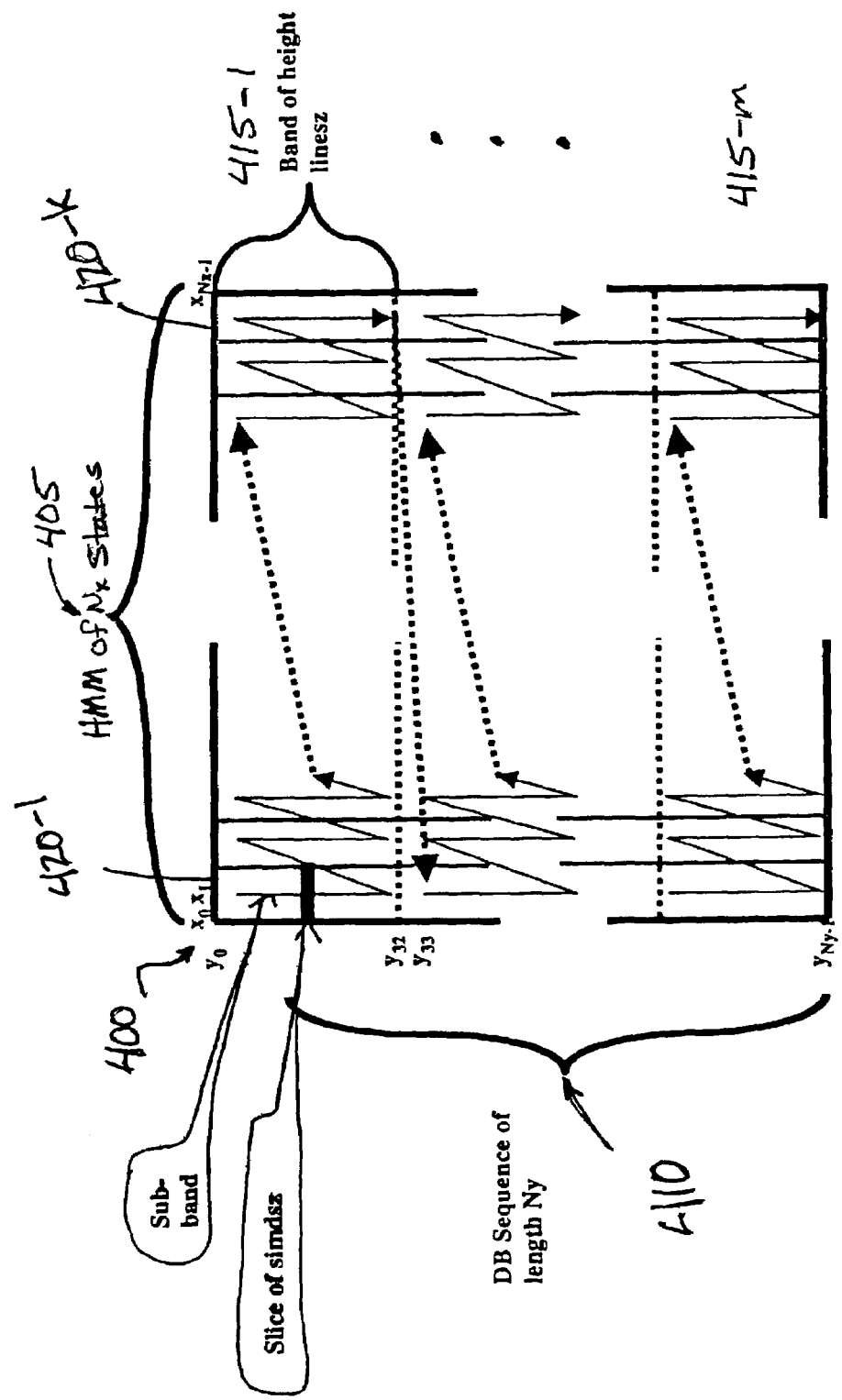
FIG. 4 shows the sequencing of the Hidden Markov Model processing, in accordance with an embodiment of the present invention.

FIG. 4 shows an embodiment of the order of comparison in the Hidden Markov Model processing according to the present invention. In FIG. 4, a matrix of the sequences 400 is shown where coordinates $x_0$ to $X_{Nx-1}$ 405 of a query sequence length Nx may extend in the horizontal direction, and coordinates $y_0$ to $y_{Ny-1}$ 410 of a database sequence length Ny may extend in the vertical direction. In FIG. 4, the matrix may be divided into a plurality of bands 415-1 to 415-m, where each band may have a length of Nx and a width of linesz. As shown in FIG. 4, each band may be further divided into a plurality of sub-bands 420-1 to 420-k, where each sub-band may have a length of linesz and a width of simdsz.

As shown in FIG. 4, in accordance with an embodiment of the present invention, to compare a database sequence of length Ny with a Hidden Markov Model sequence of length Nx, a slice of width simdsz of the database sequence and the Hidden Markov Model sequence may be compared to each other. The comparison may begin at the top of the left-most sub-band and proceed down to the bottom of the left-most sub-band. The comparison may continue from the next sub-band across to the right-most sub-band of the band, at which point starting with the top band, and proceeding down to the bottom band. The elements in each slice are processed concurrently.

A mathematical representation of a simplified variation of the Hidden Markov Model algorithm may be illustrated as:

$$\text{Dist}(i,j)=\min\{(\text{Dist}(i-1,j)+a\text{Prob}(j,j),(\text{Dist}(i-1,j-1)+ a\text{Prob}(j,j-1),(\text{Dist}(i-1,j-2)+a\text{Prob}(j,j-2))\},b\text{Prob}(j,k(i));$$

$$\text{Dist}(i,j+1)=\min\{(\text{Dist}(i-1,j+1)+a\text{Prob}(j+1,j+1),(\text{Dist}(i-1,j)+a\text{Prob}(j+1,j),(\text{Dist}(i-1,j-1)+a\text{Prob}(j+1,j-1))\},b\text{Prob}(j+1,k(i));$$

$$\text{Dist}(i,j+2)=\min\{(\text{Dist}(i-1,j+2)+a\text{Prob}(j+2,j+2),(\text{Dist}(i-1,j+1)+a\text{Prob}(j+2,j+1),(\text{Dist}(i-1,j)+a\text{Prob}(j+2,j))\},b\text{Prob}(j+2,k(i)); \text{ and}$$

$$\text{Dist}(i,j+3)=\min\{(\text{Dist}(i-1,j+3)+a\text{Prob}(j+3,j+3),(\text{Dist}(i-1,j+2)+a\text{Prob}(j+3,j+2),(\text{Dist}(i-1,j+2)+a\text{Prob}(j+3,j+2))\},b\text{Prob}(j+2,k(i));$$

where:

Dist is a score matrix that accumulates the similarity score of sequences being matched. In particular, a score is the measure of similarity of two sequences and the score matrix is used to compute the score. The above formulas describe the process of computation of the matrix elements as a function of previously computed elements of the same matrix;

aProb is a cost matrix, where element aProb(i,j) of the matrix is equal to the "cost" of either match or mismatch between elements of two sequences; and bProb is a matrix of output probabilities, where element bProb(j,t) is equal to the probability of symbol t in the state j.

In accordance with an embodiment of the present invention, a pseudo-code of the Smith-Waterman implementation discussed above may be as follows:

```
Initialize processing of query sequence;
For each sequence sx of DB {
    initiate asynchronous read from disk to memory of DB sequence
    following sx;
    check sx read completion and initialize processing of sx;
```

-continued

```
    for each band bx of sx {
        initialize processing of band bx;
        for each sub-band sbx of bx {
            prefetch temporally HMM arrays for next iteration
            prefetch next line of sx non-temporally and then tickle it every
            iteration;
            process each slice of bx process slice
        }
    }
}
```

Likewise, in accordance with an embodiment of the present invention, a detailed pseudo-code representation of the Hidden Markov Model discussed above, with the SSE™ instructions to be used in real code indicated in comments, may be as follows:

Designations linesz—cache line size in bytes. In pseudo code linesz is assumed to be 32, although algorithm is applicable to other sizes linesz16b—cache line size in 16b words Nal—size of alphabet, e.g Nal is 20 for protein. Elements of Y are in the range 0 . . . . Nal−1 short bProb[Nx/simdsz, Nal, simdsz]—output probabilities, represented in such a way that bProb[sbx, $y_i$,0:simdsz] is 64b word containing output probabilities of sub-band sbx if input symbol is $y_i$. Simplifying assumpitons: Nx is multiple of linesz and simdsz short*bProb$_{sbx}$ short aProb0[Nx], aProb1[Nx], aProb2[Nx]—transition probabilities between states[j,j], [j,j−1], [j,j−2]

short Temp0[linesz], Temp1[linesz]—vectors for temporary values char Ybuf0[Ny],Ybuf1[Ny]—buffers for database sequence. Simplifying assumptions: Ny is multiple of line size char *Y—pointer to current buffer 64b (16×4) register aProb$_j$, aprob$_{j−1}$, aProb$_{j−2}$, Accum$_j$, ShiftedAccum$_{j−1}$, ShiftedAccum$_{j−2}$ Pseudo Code

```
Initialize processing of HMM;
For each sequence sx of DB {
    initiate asynchronous read from disk to empty buffer of
    DB sequence following sx;
    check sx read completion and initialize processing of sx (Y
    points to full buffer);
    % for each band bx of sx {
    for (k=0; k<=Ny−1; k+=simdsz)
        Initialize processing of band bx;
        Restore Accum_j;
        Initialize Temp0, Temp1
        bProb_sbx=bProb;
        %for each sub-band sbx of bx {
        for (sbx=0; sbx<=Nx/simdsz−1; j++) {
            bProb_sbx+= Nal*simdsz; %pointer to vector of
            bProb[sbx,0:Nal, 0:4]
            %prefetch temporally all the lines of bProb for
            next iteration;
            temporal (bProb_sbx+ Nal*simdsz); % SSE: PREFETCHT
            temporal (bProb_sbx+ Nal*simdsz+linesz16b); % SSE:
            PREFETCHT
            temporal (bProb_sbx+ Nal*simdsz+2*linesz16b); % SSE:
            PREFETCHT
            temporal (bProb_sbx+ Nal*simdsz+3*linesz16b); % SSE:
            PREFETCHT
            temporal (bProb_sbx+ Nal*simdsz+4*linesz16b); % SSE:
            PREFETCHT
            %compute transition probabilities
            aProb_j= aProb0[sbx*simdsz:simdsz];
            aProb_{j−1}= aProb1[sbx*simdsz:simdsz];
            aProb_{j−2}= aProb2[sbx*simdsz:simdsz];
            %prefetch temporally aProb for next iteration;
            temporal (aProb0+ (sbx+1)*simdsz); %SSE: PREFETCHT
            temporal (aProb1+ (sbx+1)*simdsz); %SSE: PREFETCHT
            temporal (aProb2+ (sbx+1)*simdsz); %SSE: PREFETCHT
            %prefetch next line of sx non-temporally, and then
            tickle it every iteration;
            non-temporal (Y+k+linesz); %SSE: PREFETCHNTA
            Initialize Restore Accum_j from restored
            %for each slice of bx process slice
            for (i=k; i<=k+linesz−1; i++) {
                ShiftedAccum_{j−1}=[Temp[i], Accum[0], Accum[1],
                Accum[2]] %SSE: PSLL,
            PINSRW
                ShiftedAccum_{j−2}=[Temp0[i], Temp1[i], Accum[0],
                Accum[1]] %SSE: PSLL,
            PINSRW
                Accum_j = min(Accum_j + aProb_j, ShiftedAccum_{j−1}+
                aProb_{j−1}, ShiftedAccum_{j−2}+
                aProb_{j−2},)+ bProb_sbx[Y[i],0:4];%SSE:
                SIMD:PADDSW, PMIN
                Temp0[i]= Accum_j[2]%SSE: PEXTRW
                Temp1[i]= Accum_j[3]%SSE: PEXTRW
            };
            Save last Accum_j
        }
    }
}
```

It should be appreciated that the above-described system of the present invention can be extended to processor systems having three or more caches. That is, it should be appreciated that data system 100 of the present invention may not be limited to only have first cache 140 and second cache 160. In such an extended system, the data may be transferred from system memory 120 to the fastest cache for example, first cache 140, and then to the slowest cache, for example, second cache 160. In general, the slower caches are also the larger caches. By using multiple different caches, it is possible to increase the percentage of time data system 100 is computing and minimize the time processor 180 may spend transferring data. The increased percentage of time spent processing may significantly reduce the time needed to complete a given task.

While certain embodiments have been described and shown in the accompanying drawings, it is to be understood that such embodiments are merely illustrative of and not restrictive of the broad invention. In particular, it is noted that the described pipelining of data can be extended through many cache layers rather than the two and three cache systems described. Thus this invention should not be limited to the specific constructions and arrangements shown and described, since various other modifications may occur to those ordinarily skilled in the art, but to the claims which follow.

What is claimed is:

1. A method to stream processing of biological sequence matching in a system, the method comprising:
    prefetching by a cache controller non-temporal biological sequence data from a system memory to a first cache of a processor, wherein said prefetching bypasses a second cache memory;

prefetching by the cache controller temporal biological sequence data from the system memory to the second cache of the processor;

transferring the temporal data from the second cache memory to the first cache memory;

comparing the non-temporal biological sequence data to the transferred temporal biological sequence data in the first cache memory, wherein the comparison is performed by a rigorous matching algorithm;

determining a measure of similarity between compared biological sequence data;

saving intermediate results of said determining operation in a processor; and outputting final results of the comparing operations from the saved intermediate results by the processor.

2. The method of claim 1, wherein outputting the temporal data to the second cache from the system memory being independent from outputting the temporal data to the first cache from the second cache.

3. The method of claim 1, further comprising concurrently reading a new data input to the system memory from a disk and outputting a previously read new data input to one of the first and second caches from the system memory.

4. The method of claim 1, further comprising overlapping inputting the non-temporal data to the first cache, inputting the temporal data to the second cache, outputting the temporal data to the first cache, and processing the non-temporal data and the temporal data.

5. The method of claim 1, further comprising storing intermediate processing results in registers.

6. The method of claim 1, further comprising attaching a task to at least one of the first cache and the second cache, and when the attached task is completed, dispatching a subsequent task.

7. A method to stream processing of biological sequence matching in a system, the method comprising:

receiving a query sequence by the system memory;

receiving a plurality of biological data sequences from a biological sequence database by the system memory;

concurrently performing the following operations in a processor:

prefetching by the cache controller the query sequence from the system memory into a first cache memory of the processor, wherein said prefetching bypasses a second cache memory;

prefetching by the cache controller the plurality of biological data sequences from the system memory into the second cache memory of the processor;

transferring at least a portion of the query sequence to the second cache memory from the first cache memory;

comparing the transferred query sequence with each of the plurality of biological data sequences from the database in the second cache memory of the processor, wherein the comparison is performed by a rigorous matching algorithm; and saving intermediate results of the comparing operations in the processor; and outputting by the processor final results of the comparing operations from the saved intermediate results.

8. The method of claim 7 wherein said prefetching the query sequence, comprises:

prefetching the query sequence sections.

9. The method of claim 7 the wherein said prefetching the plurality of biological data sequences, for each biological data sequence, comprises:

prefetching the biological data sequence in sections.

10. A computer storage medium comprising a computer program, said computer program being executable by a processor to perform a method for streaming processing of biological sequence matching in a system comprising a system memory, a plurality of memory caches coupled to a cache controller; the method comprising:

receiving a query sequence by the system memory;

receiving a plurality of biological data sequences from a biological sequence database by the system memory;

concurrently performing the following operations in a processor:

prefetching by the cache controller the query sequence from the system memory into a first cache memory of the processor, wherein said prefetching bypasses a second cache memory;

prefetching by the cache controller the plurality of biological data sequences from the system memory into the second cache memory of the processor;

transferring at least a portion of the query sequence to the second cache memory from the first cache memory;

comparing the transferred query sequence with each of the plurality of biological data sequences in the second cache memory of the processor, wherein the comparison is performed by a rigorous matching algorithm; and saving intermediate results of the comparing operations in the processor; and outputting by the processor final results of the comparing operations from the saved intermediate results.

11. The machine-readable medium of claim 10 wherein said prefetching the query sequence comprises:

prefetching the query sequence in sections.

12. The machine-readable medium of claim 10 wherein said prefetching the plurality of biological data sequences, for each biological data sequence, comprises:

prefetching the biological data sequence in sections.

* * * * *